United States Patent [19]

Foguet et al.

[11] Patent Number: 4,843,165

[45] Date of Patent: Jun. 27, 1989

[54] PROCESS FOR PREPARING A 2,3-DIHYDRO-1H-IMIDAZOLYL-ETHOXY INDENE ANTITHROMBOTIC AGENT AND ITS PHARMACEUTICALLY ACCEPTABLE SALTS

[75] Inventors: Rafael Foguet; Ernesto Forne; Aurelio Sacristan; Josep M. Castello; José A. Ortiz, all of Barcelona, Spain

[73] Assignee: Ferrer Internacional S.A., Barcelona, Spain

[21] Appl. No.: 135,040

[22] Filed: Dec. 18, 1987

[30] Foreign Application Priority Data

Jan. 14, 1987 [ES] Spain ................................... 8700155

[51] Int. Cl.$^4$ ............................................ C07D 233/60
[52] U.S. Cl. ................................................. 548/341
[58] Field of Search ........................................ 548/341

[56] References Cited

U.S. PATENT DOCUMENTS 4,769,468  9/1988  Georgien et al. ................... 548/341

Primary Examiner—Mary C. Lee
Assistant Examiner—J. Richter
Attorney, Agent, or Firm—Michael J. Striker

[57] ABSTRACT

A process is disclosed for preparing a 2,3-dihydro-1H-imidazolylethoxy indene antithrombotic agent and its pharmaceutically acceptable salts.

4 Claims, No Drawings

PROCESS FOR PREPARING A 2,3-DIHYDRO-1H-IMIDAZOLYL-ETHOXY INDENE ANTITHROMBOTIC AGENT AND ITS PHARMACEUTICALLY ACCEPTABLE SALTS

BACKGROUND OF THE INVENTION

This invention relates to a novel process for obtaining a 2,3-dihydro-1H-imidazolylethoxy indene antithrombotic agent and its pharmaceutically acceptable salts.

The 2,3-dihydro-1H-imidazolylethoxy indene compounds which are useful as antithrombotic agents and process for preparing such compounds as disclosed and described in U.S. Pat. No. 4,610,998.

The process for this invention differs from that disclosed in the aforementioned Spanish patent in that the starting compound is 5-methoxy-1-indanone which, through its cyanohydrin, leads to 2,3-dihydro-5-methoxy-1H-inden-1-carboxylic acid followed by subsequent dimethylation of the methoxy group, protection of the carboxylic group by esterification, formation of the corresponding 2-chloroethyl ether, reaction with imidazole and final hydrolysis. This process is more advantageous than that described in the aforementioned Spanish patent because it allows to handle crude materials under a high purity, which results in an elevated yield.

DETAILED DESCRIPTION OF THE INVENTION

The process of this invention is directed to the preparation of 2,3-dihydro-5-[β-(1H-imidazol-1-yl)ethoxy]-1H-indene-1-carboxylic acid and its pharmaceutically acceptable salts. A preferred pharmaceutically acceptable salt is hydrochloride. All the intermediates used in this invention are new and will be subject matter of the present invention.

The process of the invention is illustrated in the following Reaction Scheme wherein preferred reactants are shown to more clearly illustrate the process of the invention.

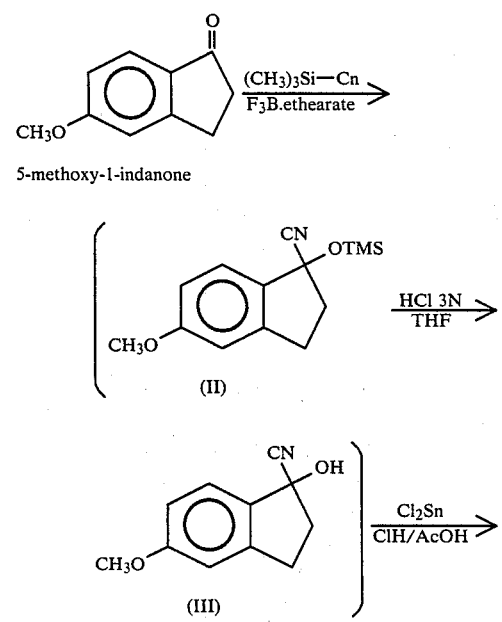

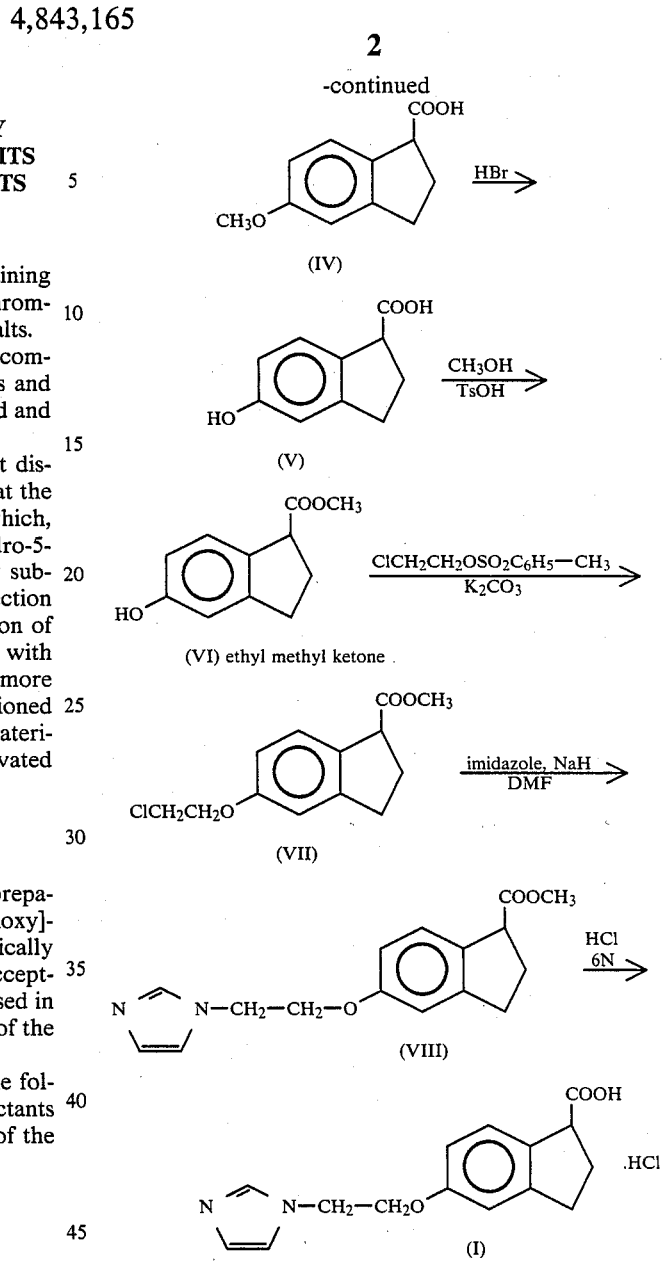

With reference to the Reaction Scheme, 5-methoxy-1-indanone, which can be prepared by oxidation from 2,3-dihydro-5-methoxy-1H-indene with chromic anhydride in aqueous solution of glacial acetic acid, was reacted with trimethylsilylcyanide and in the presence of a Lewis acid as a catalyzer at a temperature ranging from 70° C. to 120° C. Thus, suitable catalyzers are boron trifluoride ethearate, zinc iodide and aluminium trichloride.

The acid hydrolysis of 2,3-dihydro-5-methoxy-O-(trimethylsilyl)-1H-inden-1-one cyanohydrin (III) which, like its precursor, does not require any purification to proceed with the process. This hydrolysis was performed with a mineral acid and in an ethereal medium followed by heating at a temperature ranging from 40° C. to boiling temperature of the mixture. Hydrochloric acid is preferred as a mineral acid and tetrahydrofuran as an ethereal solvent.

The conversion of the aforesaid cyanohydrine into 2,3-dihydro-5-methoxy-1H-inden-1-carboxylic acid (IV) was made with stannous chloride in acid medium composed of concentrated hydrochloric acid and glacial acetic acid at a temperature ranging from 80° C. to 110° C.

By demethylation of 2,3-dihydro-5-methoxy-1H-inden-1-carboxylic acid (IV) with hydrobromic acid at a temperature ranging from 130° C. to boiling temperature of the mixture, 2,3-dihydro-5-hydroxy-1H-inden-1-carboxylic acid (V) was obtained. This acid, by reaction with an aliphatic alcohol in the presence of a sulphonic acid as a catalyzer, led to the corresponding ester. A preferred aliphatic alcohol is methanol. p-Toluensulphonic acid is preferably used as a catalyzer in this esterification. It is convenient that this esterification be carried out at boiling temperature of the mixture. Thus, methyl 2,3-dihydro-5-hydroxy-1H-inden-1-carboxylate (VI) was obtained.

The reaction of the aforesaid ester with a 2-chloroethyl sulphonate in the presence of a base selected from alkaline or earthalkaline carbonates or bicarbonates at boiling temperature of the mixture gave the β-chloroethylderivative, chemically, methyl 2,3-dihydro-5-(β-chloroethoxy)-1H-inden-1-carboxylate (VII). The selected base is potassium carbonate. An inert medium, specifically an aliphatic ketone, i.e., methyl ethyl ketone was selected as a solvent.

The alkylation of imidazole with ester (VII) in a suitable solvent and in the presence of sodium hydride at boiling temperature of the mixture led to methyl 2,3-dihydro-5-[β-(1H-imidazol-1-yl)ethoxy]-1H-inden-1-carboxylate (VIII). Low-molecular weight N,N-disubstituted linear amides were selected as a solvent, being dimethyl formamide preferred.

The subsequent hydrolysis of the preceding ester with a mineral acid at boiling temperature of the mixture gave the compound of the present invention, 2,3-dihydro-5-[β-(1H-imidazol-1-yl)ethoxy]-1H-inden-1-carboxylic acid (I). Hydrochloric acid was used as mineral acid so as to obtain the compound of this invention in the form of hydrochloride which is the preferred pharmaceutically acceptable salt.

The following examples are provided to further illustrate the invention, but they are not to be construed as being limitative of the invention. Unless otherwise indicated, all temperatures are in degrees Celsius.

EXAMPLE 1

2,3-Dihydro-5-methoxy-1H-indene

In a 250-liter stainless steel reactor (Pilot Plant) 6.81 kg of 97% sodium hydroxyde in 100 l of distilled water were dissolved, and heating at 17° C., 22 kg of 2,3-dihydro-1H-inden(5-indanol) were added in the course of 20 min and then stirred to total dissolution. 20.13 kg of recently-distilled dimethyl sulphate were added through a funnel for about 1 hour. Then the mixture was refluxed for 8 hours and allowed to cool. The upper organic phase was decanted, the aqueous phase was extracted twice with 5 l of toluene, the organic phases were washed with 10% sodium hydroxyde solution, with water and the solvent was distilled at vacuum to give 18.7 kg (77%) of colourless liquid. GLC 99%; $n_D^{20} = 1.5430$; IR and $^1$H-NMR spectra were consistent with structure.

$^1$H-NMR Spectrum (CDCl$_3$), ppm: 2.1 (m, 2H; —CH$_2$—), 3.85 (m, 4H; Ar $>$(CH$_2$)$_2$—), 3.74 (s, 3H; —OCH$_3$), 6.55–6.88 (m, 2H; Ar—) and 7.08 (d, 1H, $J_o = 8$ Hz; Ar—).

EXAMPLE 2

5-methoxy-indanone

In a 250-liter stainless steel reactor (Pilot Plant) containing 9.45 kg of 2,3-dihydro-5-methoxy-1H-indene in 54 l of glacial acetic acid cooled at 5°–10° C., 10.08 kg of chromic anhydride (1.58 equivalents) dissolved in 5 l of water and 27.5 l of glacial acetic acid were added for 4.5–5 hours at 5°–10° C. Then, the mixture was kept at 5° C. for further 5 hours and at room temperature overnight under stirring. The reaction mixture was poured, under vigorous stirring, onto 800 l of water cooled at 5° C. and 5-methoxy-1-indanone precipitated (as supernatant). The precipitate was filtered by centrifugation, washed with 30 l of water, centrifugated again and dried to constant weight to give 6.83 kg (66%) of yellow solid. M.p. 108°–110° C.; GLC 98.9%; water content (KF): lower than 0.1%; IR and $^1$H-NMR spectra were consistent with structure.

IR Spectrum (KBr), cm$^{-1}$: 3060–2840, 1690, 1600, 1250, 1095, 840.

$^1$H-NMR Spectrum (CDCl$_3$), ppm: 2.5–2.75 (m, 2H; —CH$_2$—), 2.9–3.2 (m, 2H; —CH$_2$—); 3.85 (s, 3H; —OCH$_3$), 6.88 (m, 2H; Ar—) and 7.67 (d, 1H, $J_o = 8$ Hz; Ar—).

EXAMPLE 3

2,3-Dihydro-5-methoxy-O-(trimethylsilyl)-1H-inden-1-one cyanohydrin (II)

22.28 g of 5-methoxy-1-indanone were introduced into a 20-liter reactor provided with a mechanical stirrer, addition funnel, thermometer and cooling tower which outlet was successively connected to a tower drier and a gas absorption tower loaded with sodium hydroxide solution. The system was subjected to nitrogen drain and when stabilized in this manner, 1.5 kg of trimethylsilylcyanide (1.1 equivalents) and 15 ml of boron trifluoride ethearate were rapidly poured through the funnel. Then, the reactor was immersed in a previously-heated oil bath (80° C.). After 45 minutes, the reaction mass started to soften and stirring was on; the temperature was kept at 75°–80° C. for 2 hours and at 100° C. for further 2 hours. After overnight at room temperature under nitrogen atmosphere, the resulting oil liquid was characterized by respective IR and $^1$H-NMR spectra.

IR Spectrum (film), cm$^{-1}$: 3020–2840, 2730 (weak), 1485, 1250, 1080, 875, 840.

$^1$H-NMR Spectrum (CDCl$_3$), ppm: 0.27 (s, 9H; Si(CH$_3$)$_3$), 2.0–3.0 (multiple bands, 4H; (—CH$_2$)$_2$—), 3.55 (s, 3H; CH$_3$O—), 6.38–6.88 (m, 2H; Ar—) and 7.22 (d, $J_o = 8$ Hz, 1H; Ar—).

EXAMPLE 4

2,3-Dihydro-5-methoxy-1H-inden-1-one cyanohydrin (III)

In the same reactor as prepared for trimethylsilylcyanohydrin in Ex. 3, 3.7 l of tetrahydrofurane and through the funnel 3375 ml of 3N hydrochloric acid were added, a slight exothermia occurred till reaching 40° C. When the exothermia became stabilized, the reaction mixture was heated in oil bath at 66°-70° C. for 1 hour, then it was allowed to cool at room temperature, 3375 of water were added, the organic phase was decanted and the aqueous phase was extracted twice with 3 l of toluene. The combined organic extracts were concentrated to dryness at vacuum. The oily residue was solidified under vacuum stove to give 2.3 kg (88.5%) of cyanohydrin.

IR Spectrum (film), cm$^{-1}$: 3420, 3020-2820, 2220 (intense), 1475, 1295, 1250, 1110, 1015, 840, 810.

$^1$H-NMR Spectrum (CDCl$_3$), ppm: 2.4-3.1 (wide, 4H; —(CH$_2$)$_2$—), 3,50 (s, 1H; —OH), 3.80 (s, 1H; CH$_3$O—), 6.6-7.15 (multiple bands, 2H; Ar—) and 7.37 (d, 1H, J$_o$=8 Hz; Ar—).

EXAMPLE 5

2,3-Dihydro-5-methoxy-1H-inden-1-carboxylic acid (IV)

In a 100-liter glass reactor (Pilot Plant) connected to a gas absorption tower containing sodium hydroxyde solution, 16.3 l of concentrated hydrochloric acid, 7.14 kg of dihydrate stannous chloride and 14 l of glacial acetic acid were added under heating till the reaction mass reached 90° C. Then, 2.3 kg of 2,3-dihydro-5-methoxy-1H-inden-1-one cyanohydrin dissolved in 10 l of glacial acetic acid were added and heated at 100°-105° C. for 10 hours. The mixture was allowed to cool down to 50° C., 20 l of toluene and 30 l of water were added and stirred for 1 hour. The aqueous phase was decanted, the insoluble material was filtered and washing with toluene the residue was rejected; then it was extracted twice with 18 l of toluene and filtered if necessary. The filtered organic extracts were washed twice with 35 l of sodium chloride saturated solution and once with water, then evaporated to dryness at vacuum; the residue, as brown semisolid, was a mixture of carboxylic acid and ketone weighing 2.3 kg. It was taken in 25 l of toluene and 15 l of 1N potassium hydroxyde solution and stirred for 30 minutes; the toluene phase was extracted for the second time with 15 l of 1N sodium hydroxyde solution. The alkaline extracts, cooled at 10° C., and 4 l of methylene chloride were acidified with 6N hydrochloric acid, further 6 l of methylene chloride were added and the organic phase was separated; the aqueous phase was extracted twice with 10 l of methylene chloride, and the organic extracts were washed several times with sodium chloride saturated solution (diluted with water), dried over magnesium sulphate and concentrated to dryness at vacuum. The residue as brown solid weighed 1.6 kg (69%), m.p. 111°-116° C., acid grou titration: 96%, and was crystallized from acetonitrile, m.p. 118°-121° C.

IR Spectrum (KBr), cm$^{-1}$: 3300-2400, 1700, 1480, 1420, 1315, 1260, 1170, 1140, 1090, 1030, 860, 790.

$^1$H-NMR Spectrum (CDCl$_3$), ppm: 2.2-3.2 (2 multiplets, 4H; —(CH$_2$)$_2$—), 3.74 (s, 1H; CH$_3$O—), 3.98

(t, 1H, J = 7Hz; $>$CH—), 6.6-6.87 (multiple bands, 2H; Ar—) and 7.27 (d, 1H, J$_o$=8 Hz; Ar—).

EXAMPLE 6

2.3-Dihydro-5-hydroxy-1H-inden-1-carboxylic acid (V)

In a 20-liter reactor provided with a mechanical stirrer, 1.6 kg of 2,3-dihydro-5-methoxy-1H-inden-1-carboxylic acid and 8 l of 48% hydrobromic acid were introduced and heated at 135°-140° C. in oil bath for 15 hours. The mixture was allowed to cool, and the hydrobromic acid was evaporated at vacuum; to the blackish residue, 3 l of toluene were added and the solvent was evaporated at vacuum. This operation was made again with further 3 l of toluebe to give the desired compound as blackish solid, 1.5 kg (100%), m.p. 137°-138° C. and acid group titration: 101%.

IR Spectrum (KBr), cm$^{-1}$: 3600-2600, 1710, 1610, 1500, 1460, 1230, 1180, 855, 820, 755.

$^1$H-NMR Spectrum (d$_6$-DMSO), ppm: 2.0-3.0 (2 multiplets, 4H; —(CH$_2$)$_2$—), 3.81

(t, 1H, J = 7Hz; $>$CH—), 6.5-6.75 (m, 2H; Ar—), 7.08 (d, 1H, J$_o$=8 Hz; Ar—) and 8.75 (wide, 2H; —OH and —COOH).

EXAMPLE 7

Methyl 2,3-dihydro-5-hydroxy-1H-inden-1-carboxylate (VI)

In a 20-liter reactor with a mechanical stirrer, 1.6 kg of 2,3-dihydro-5-hydroxy-1H-inden-1-carboxylic acid were dissolved with 7.2 l of absolute methanol, 9 g of p-toluenesulphonic acid were added and then refluxed under stirring in oil bath heated at 90° C. for 24 hours. The mixture was allowed to cool, the excess of methanol was evaporated at vacuum, the residue was diluted with 1.5 l of water, 1.5 l of sodium bicarbonate saturated solution and 5 l of toluene and then stirred for 30 minutes. The insoluble material was filtered, washed twice with 1 l of toluene; the aqueous phase was extracted with 2 l of toluene, and the organic phases were filtered using a filter paper and washed with water. The toluene phase was concentrated at vacuum to give a blackish, viscous liquid residue weighing 1.391 kg (88%), which was distilled at vacuum to give 1.1 kg (70%) of colourless liquid at 124°-137° C./0.03-0.025 tors, n$_D^{20}$=1.5533, IR and $^1$H-NMR spectra were consistent with structure.

IR Spectrum (film), cm$^{-1}$: 3400, 3040-2840, 1710, 1490, 1450, 1340, 1260, 1210, 1170, 850, 810.

$^1$H-NMR Spectrum (CDCl$_3$), ppm: 2.1-3.1 (2 multiplets, 4H; —(CH$_2$)$_2$—), 3.70 (s, 3H; —COOCH$_3$), 3.96

(t, 1H; J = 6.5Hz; $>$CH—), 5.95 (s, 1H; —OH), 6.5-6.75 (m, 2H; Ar—) and 7.15 (d, 1H, J$_o$=8 Hz; Ar—).

EXAMPLE 8

Methyl 2,3-dihydro-5-($\beta$-chloroethoxy)-1H-inden-1-carboxylate (VII)

In a 20-liter reactor provided with a mechanical stirrer and reflux cooler, 1078 g of methyl 2,3-dihydro-5-hydroxy-1H-inden-1-carboxylate were dissolved with 9 l of dry methyl ethyl ketone, 1162 g of anhydrous potassium carbonate were added and stirred for 30 minutes; then 1448 h of 2-chloroethyl p-toluensulphonate were added and refluxed in oil bath for 50 hours. The mixture was allowed to cool, the insoluble solid was filtered and washed twice with acetone over the same filter. The filtrate was evaporated and dried at vacuum, the residue was dissolved in 4.7 l of toluene and extracted with 1.8 l of 3N sodium hydroxyde solution through the decantation funnel and mechanical stirring for 15 minutes; then it was neutralized with water and dried. After evaporation of solvent at vacuum, the residue as reddish liquid weighed 1419 g (99%). Thin-layer chromatography (silica-gel) showed a major spot and a slight shadow at lower Rf. Cl analysis correct. It was used for the following synthesis step without further purification.

IR Spectrum (film), cm$^{-1}$: 3020–2860, 1730, 1610, 1490, 1435, 1270, 1170, 1040, 810.

$^1$H-NMR Spectrum (CDCl$_3$), ppm: 2.2–3.2 (2 multiplets, 4H; —(CH$_2$)$_2$), 3.68 (s+t, 5H; —COOCH$_3$ and —CH$_2$Cl), 3.98

(t, 1H, J = 7Hz; $>$CH—), 4.19 (t, 2H, J=6 Hz; —OCH$_2$—), 6.65–6.8 (m, 2H; Ar—) and 7.26 (d, 1H, J$_o$=8 Hz; Ar—).

EXAMPLE 9

Methyl 2,3-dihydro-5-[β-(1H-imidazol-1-yl)ethoxy]-1H-inden-1-carboxylate (VIII)

In a 20-liter reactor provided with a mechanical stirrer, reflux cooler, thermometer, compensatory pressure funnel and nitrogen atmosphere, 183.84 g of 80% sodium hydride (20% paraffin) and 2.8 l of dry dimethylformamide (4 Å sieves) were dissolved. Then a solution of 417.19 g of imidazole in 1.5 l of DMF was added under stirring and cooling at 10°–20° C. (t$_R$) in water-ice bath; after completion of the addition, the bath was withdrawn and the mixture was heated at 90°–100° C. for 30 minutes using an electrical blanket till total hydrogen liberation which allowed the formation of anion. After cooling of the mixture again at room temperature, a solution of methyl 2,3-dihydro-5-(β-chloroethoxy)-1H-inden-1-carboxylate in 4 l of DMF was added and then heated at 90°–100° C. (t$_R$) for 9 hours. After cooling, the mixture was poured to 10 l of water and 10 kg of ice under stirring and extracted twice with 5 l of methylene chloride, and the organic phases were washed with water (4 times) and neutralized. The desired compound as successively extracted with 3.2 l and 1 l of 2N hydrochloric acid and 1 l of water; the aqueous extracts were washed with 2.5 l of methylene chloride and taken to basic pH by adding 1 l of ammonium hydroxide concentrated solution under cooling. The precipitate was extracted with 3 l and 1.5 l of methylene chloride and the organic extracts were washed (3 times) with 3 l of water, dried and concentrated to dryness. The residue, as brownish oil, weighed 1264 g (79%) and thin-layer chromatography (silica-gel) showed a major spot and correct spectroscopy; it was used for the following synthesis step without further purification.

IR Spectrum (film), cm$^{-1}$: 3100–2840, 1730, 1490, 1430, 1250, 1170, 1070, 815.

$^1$H-NMR Spectrum (CDCl$_3$), ppm: 2.2–3.2 (2 multiplets, 4H; —(CH$_2$)$_2$—), 3.67 (s, 3H; —COOCH$_3$), 3.96

(t, 1H, J = 7Hz; $>$CH—), 4.20 (m, A$_2$B$_2$ system, 4H; —CH$_2$—CH$_2$—), 6.6–7.4 (multiple bands, 5H; Ar—, imidazole) and 7.55 (s, 1H; imidazole).

EXAMPLE 10

2,3-Dihydro-5-[β-(1H-imidazol-1-yl)ethoxy]-1H-inden-1-carboxylic acid hydrochloride In a 5-liter reactor provided with a mechanical stirrer and cooler, a mixture of 1264 g of methyl 2,3-dihydro-5-[β-(1H-imidazol-1-yl)ethoxy]-1H-inden-1-carboxylate and 3.5 l of 6N hydrochloric acid was refluxed, and the formed methanol (t$_R$=100°–107° C.) was removed. The mixture was allowed to cool and the hydrochloric acid was evaporated at vacuum. When stirring of the resulting mass became rather difficult, 0.8 l of benzene were added twice under vacuum distillation so as to facilitate the hydrochloric acid removal. In the same manner, 1.8 l of acetone were added and distilled till the mass started to crystallize, then further 1.8 l of acetone were added and distillation was continued to a residual volume of 2.5–3 l, and thus the mass was crystallized for the most part. After standing overnight, 1.2 l of acetone were added and refluxed for 20 minutes under stirring. The resulting yellowish solid was cooled with water-ice at 5° C., filtered, washed with the minimal quantity of cold acetone (1.5 l) and dried in 50° C.-vacuum stove under potassium-hydroxide/phosphorous pentoxide to constant weight: 1200 g (88%) of a white-yellowish solid were obtained, m.p. 170°–173° C. Recrystallized from 12 l of isopropanol under reflux, 145 ml of water and 55 g of active carbon were added. After cooling, filtering off and drying to constant weight, 981 g (72%) of a white solid were obtained, m.p. 171°–173° C. Analysis correct.

IR Spectrum (KBr), cm$^{-1}$: 3300–2400, 1680, 1480, 1266, 1220, 1080, 1040, 820, 735.

$^1$H-NMR Spectrum (d$_4$—MeOH), ppm: 2.3 and 2.9 (2m, A$_2$B$_2$ system; Ar—CH$_2$—CH$_2$—), 3.9

(t, 1H, J = 7.5Hz; $>$C$\underline{H}$—OOH), 4.32 and 4.67 (2m, A$_2$ and B$_2$ system; —CH$_2$—CH$_2$O—), 6.6–6.9 (m, 2H; Ar—), 7.24 (d, 1H; J$_o$=8.1 Hz; Ar—), 7.56 and 7.74 (2d, 2H; J=1.4 Hz; imidazole) and 9.07 (d, 1H, J=1.4 Hz; imidazole).

We claim:

1. A process for preparing a compound having the formula:

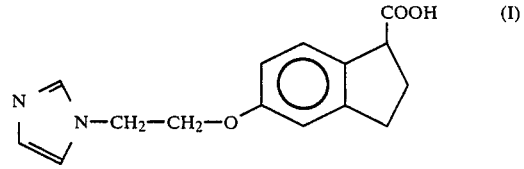

(I)

and its pharmaceutically acceptable salts; said process comprising:

(a) reacting 5-methoxy-1-indanone with trimethylsilylcyanide in the presence of a Lewis acid as a catalyzer to obtain the O-trimethylsilyl cyanohydrine having the formula:

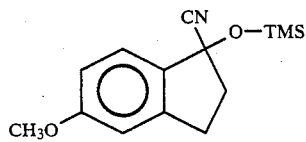
(II)

(b) subjecting said O-trimethylsilyl cyanohydrine (II) to acid hydrolysis to obtain the cyanohydrine having the formula:

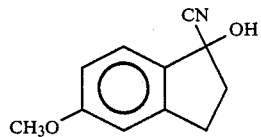
(III)

(c) reacting said cyanohydrine (III) with stannous chloride in acid medium to obtain the carboxylic acid having the formula:

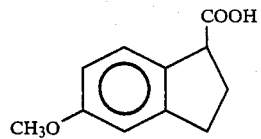
(IV)

(d) subjecting said carboxylic acid (IV) to demethylation with hydrobromic acid to obtain the carboxylic acid having the formula:

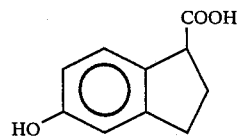
(V)

(e) reacting said carboxylic acid (V) with an aliphatic alcohol having the formula:

ROH     (V')

wherein R is an aliphatic alkyl of 1-4 carbon in the presence of a sulphonic acid as a catalyzer to obtain an ester having the formula:

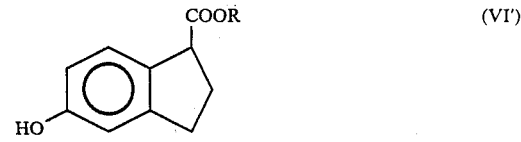
(VI')

wherein R is as defined above;

(f) reacting said ester (VI') with a 2-chloroethyl sulphonate in the presence of an alkaline or earthalkaline carbonate or bicarbonate to obtain an ester having the formula:

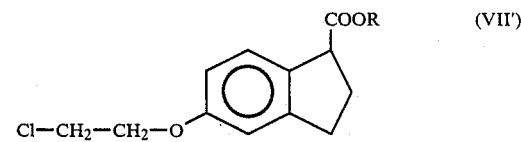
(VII')

wherein R is as defined above;

(g) reacting said ester (VII') with imidazole and sodium hydride as a coadjuvant to obtain an ester having the formula:

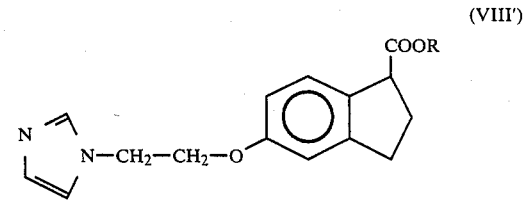
(VIII')

wherein R is as defined above; and (h) subjecting said ester (VIII') to acid hydrolysis to obtain said Formula I compound.

2. The process of claim 1 wherein R is methyl.

3. The process of claim 1 wherein the last mentioned acid hydrolysis is made with hydrochloric acid.

4. The process of claim 1 wherein the pharmaceutically acceptable salts are hydrochloride.

* * * * *